United States Patent
Duncan et al.

(10) Patent No.: US 10,376,240 B2
(45) Date of Patent: Aug. 13, 2019

(54) CONTRAST AGENT SENSITIVE MEDICAL ULTRASOUND IMAGING

(71) Applicant: Siemens Medical Solutions USA, Inc., Malvern, PA (US)

(72) Inventors: David P. Duncan, Renton, WA (US); Xiaozheng Zeng, Sammamish, WA (US); Ismayil M. Guracar, Redwood City, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 554 days.

(21) Appl. No.: 14/713,810

(22) Filed: May 15, 2015

(65) Prior Publication Data

US 2016/0331350 A1  Nov. 17, 2016

(51) Int. Cl.
*A61B 8/00* (2006.01)
*A61B 8/08* (2006.01)

(52) U.S. Cl.
CPC .............. *A61B 8/481* (2013.01); *A61B 8/488* (2013.01); *A61B 8/5223* (2013.01); *A61B 8/54* (2013.01)

(58) Field of Classification Search
CPC ..... A61B 8/481; A61B 8/5238; A61B 8/5246; A61B 8/488; A61B 8/5223; A61B 8/54
See application file for complete search history.

(56) References Cited

U.S. PATENT DOCUMENTS

| | | | |
|---|---|---|---|
| 5,873,829 A | 2/1999 | Kamiyama et al. | |
| 6,010,456 A | 1/2000 | Rhyne | |
| 6,050,944 A | 4/2000 | Holley et al. | |
| 6,213,947 B1* | 4/2001 | Phillips | G01S 7/52038 600/443 |
| 6,340,348 B1 | 1/2002 | Krishnan et al. | |
| 6,436,041 B1 | 8/2002 | Phillips et al. | |
| 6,461,303 B2 | 10/2002 | Angelsen | |
| 6,494,841 B1 | 12/2002 | Thomas et al. | |
| 6,497,666 B1* | 12/2002 | Phillips | A61B 8/481 600/458 |

(Continued)

FOREIGN PATENT DOCUMENTS

| | | |
|---|---|---|
| JP | 2001299765 A | 10/2001 |
| JP | 2002-177270 | 6/2002 |

(Continued)

OTHER PUBLICATIONS

Abstract of Calliada et al., Ultrasound contrast agents: basic principles, Eur J Radiol, May 1998; 27 Suppl 2:S157-60.*

(Continued)

*Primary Examiner* — Peter Luong

(57) ABSTRACT

In contrast agent imaging, a beamformer and transducer scan a region of a patient having contrast agents. A detector detects the contrast agents with at least two different contrast agent imaging techniques from ultrasound data resulting from the scanning. A processor compares responses of the contrast agents detected between the at least two different contrast agent imaging techniques and selects a relative contribution of the at least two different contrast agent imaging techniques. The selection is based on the comparing. Contrast agent imaging of the patient is performed using at least one of the contrast agent imaging techniques. The performance is based on the selected relative contribution.

10 Claims, 2 Drawing Sheets

(56) References Cited

U.S. PATENT DOCUMENTS

| | | | |
|---|---|---|---|
| 6,503,203 B1 | 1/2003 | Rafter et al. | |
| 6,579,238 B1 | 6/2003 | Simopoulos et al. | |
| 6,599,248 B1* | 7/2003 | Tamura | A61B 8/06 600/454 |
| 6,602,195 B1* | 8/2003 | Krishnan | G01S 7/52039 600/447 |
| 6,612,989 B1 | 9/2003 | Brock-Fisher | |
| 6,626,836 B2 | 9/2003 | Mao et al. | |
| 6,632,177 B1 | 10/2003 | Phillips et al. | |
| 6,679,844 B2 | 1/2004 | Loftman et al. | |
| 6,858,008 B2 | 2/2005 | Li et al. | |
| 6,899,681 B1* | 5/2005 | Phillips | G01S 7/52026 600/437 |
| 7,993,273 B2 | 8/2011 | Phillips et al. | |
| 7,998,076 B2 | 8/2011 | Philips et al. | |
| 2004/0087857 A1* | 5/2004 | Napolitano | G01S 7/52039 600/443 |
| 2005/0054928 A1* | 3/2005 | Cerofolini | A61B 8/481 600/443 |
| 2005/0055178 A1* | 3/2005 | Phillips | A61B 8/481 702/189 |
| 2006/0036174 A1* | 2/2006 | Guracar | A61B 8/481 600/458 |
| 2013/0090557 A1* | 4/2013 | Takagi | A61B 8/085 600/431 |
| 2015/0087985 A1* | 3/2015 | Yoshiara | G01S 7/52038 600/443 |
| 2016/0066888 A1* | 3/2016 | Yao | A61B 8/463 600/431 |

FOREIGN PATENT DOCUMENTS

| | | |
|---|---|---|
| JP | 2007-090075 | 4/2007 |
| JP | 2007167626 A | 7/2007 |
| JP | 2013-252182 | 12/2013 |

OTHER PUBLICATIONS

Wilkening, W.; Brendel, B.; Jiang, H.; Lazenby, J.; Ermert, H., "Optimized receive filters and phase-coded pulse sequences for contrast agent and nonlinear imaging," Ultrasonics Symposium, 2001 IEEE, pp. 1733-1737 vol. 2, 2011.

Office Action dated May 22, 2017 from counterpart Japanese application No. 2016-097474, filed May 13, 2016, 6 total pages.

Notice of Allowance dated May 8, 2018 in corresponding Japanese Patent Application No. 2016-097474.

* cited by examiner

CONTRAST AGENT SENSITIVE MEDICAL ULTRASOUND IMAGING

BACKGROUND

The present embodiments relate to contrast agent imaging. In particular, contrast agent imaging in medical ultrasound imaging systems is enhanced.

The use of contrast agents in routine clinical examinations has become more common. When imaging ultrasound contrast agents, there are different approaches. The approach with the highest contrast agent detection (sensitivity) and tissue rejection (specificity) is desired. Higher sensitivity and specificity allows good visualization of the contrast agents. Different pulse sequences, probe optimizations, and processing may produce different levels of sensitivity. However, the approach with a sufficient sensitivity and specificity may change over the course of an exam. One approach may provide sufficient sensitivity at a beginning of an exam where there is a greater concentration of contrast agents, but may falsely show a lack of contrast agents later in the exam, leaving the user with the impression that no contrast agent is left in the patient or that the system is not imaging correctly. The user either assumes the system is operating correctly or verifies contrast agent detection by switching the imaging approach to check for contrast agents detected using a different process.

BRIEF SUMMARY

By way of introduction, the preferred embodiments described below include a method and systems for medical imaging of contrast agents. Rather than relying on one approach, the ultrasound system accounts for variation in sensitivity between different approaches. For example, the ultrasound system compares measures of sensitivity of different approaches. The approach with the greater sensitivity at a given time is emphasized in the imaging for that time. As another example, a timer may be used to switch approaches where the different approaches' relative sensitivity varies inversely over time.

In a first aspect, a method is provided for medical ultrasound imaging of contrast agents. A beamformer and transducer scan a region of a patient having contrast agents. A detector detects the contrast agents with at least two different contrast agent imaging techniques from ultrasound data resulting from the scanning. A processor compares responses of the contrast agents detected between the at least two different contrast agent imaging techniques and selects a relative contribution of the at least two different contrast agent imaging techniques. The selection is based on the comparing. Contrast agent imaging of the patient is performed using at least one of the contrast agent imaging techniques. The performance is based on the selected relative contribution.

In a second aspect, a method is provided for medical ultrasound imaging of contrast agents. An ultrasound system performs a first type of contrast agent imaging during an imaging session of a patient. The imaging session is timed relative to an injection of the contrast agents into the patient. The ultrasound system switches to a second type of contrast agent imaging during the imaging session. The second type is different than the first type, and the switching is in response to the timing.

In a third aspect, a system is provided for medical ultrasound imaging of contrast agents. A transmit beamformer is configured to transmit a sequence of pulses. A receive beamformer is configured to output samples responsive to the pulses of the sequence. A contrast agent detector is configured to detect contrast agent responses from the samples using different processes. Each of the different processes uses at least one of the same samples. A processor is configured to generate contrast agent images where a ratio of the responses from the samples using the different processes in the contrast agent images varies. A display is operable to display the contrast agent images.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automatic contrast agent imaging is provided. Contrast agent images are typically generated using low-power (low-MI) pulse sequences that image the non-linear bubble behavior. Two methods that are commonly used are a 3-pulse sequence (e.g., imaging cubic fundamental response) and 2-pulse sequence (e.g., imaging second, higher order, or even harmonic response). In general, the 3-pulse sequence has been shown to have a higher level of sensitivity than the 2-pulse sequence, especially near the start of contrast agent imaging examination when large concentrations of contrast agents are present throughout the body. When imaging with the 2-pulse sequence using imaging frequencies within the resonance band of the contrast agents, the 2-pulse sequence has higher bubble sensitivity in the late portions of the examination than the 3-pulse sequence. The 3-pulse sequence sensitivity may be so low during the late phase that the user may have the impression that there is no more contrast agent present even when contrast agents are present.

Both 2-pulse and 3-pulse sequences may be used to determine the response of contrast agents. The responses are analyzed in real time for overall sensitivity levels, such as using thresholding, and the ultrasound system then automatically performs contrast agent imaging providing the higher bubble sensitivity. A specialized pulse sequence may be used to derive information for both the 2-pulse and 3-pulse approaches from the same set of data. This specialized pulse sequence is used to derive the data for the automated decision using the real-time contrast image sensitivity or exam phase.

Figure 1:
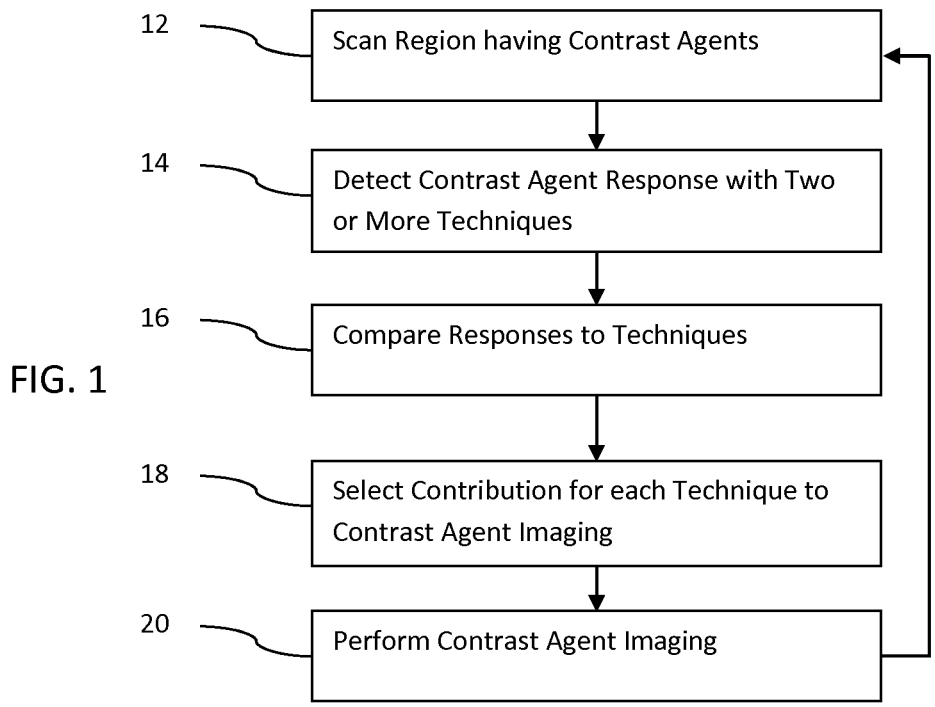
FIG. 1 is a flow chart diagram of one method for medical ultrasound imaging of contrast agents.

FIG. 1 shows one embodiment of a method for medical ultrasound imaging of contrast agents. An ultrasound system is configured to use different types of contrast agent imaging. The relative contribution of each type for the contrast agent imaging is based on a comparison of contrast agent responses.

Figure 3:
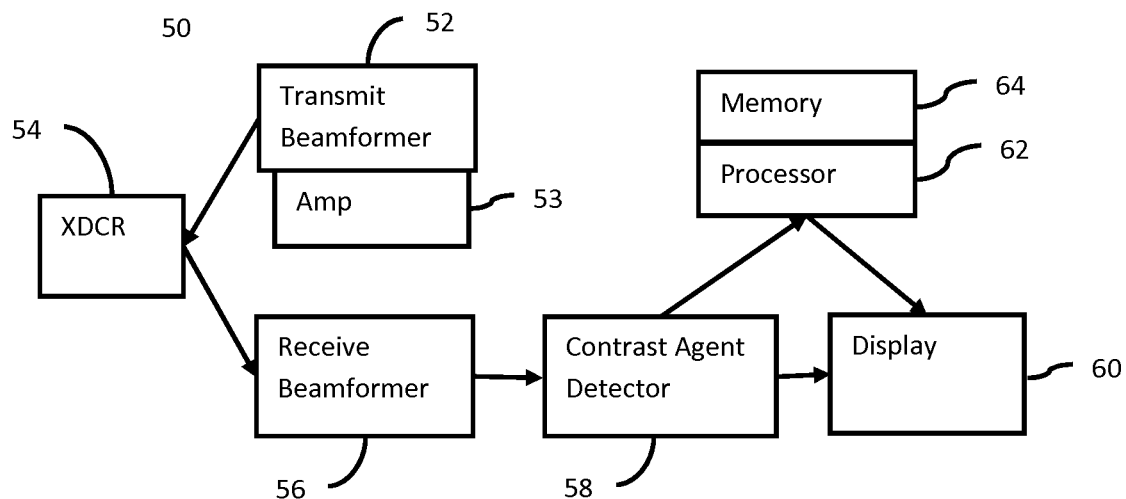
FIG. 3 is a block diagram of one embodiment of an ultrasound contrast agent imaging system.

The method is implemented by the system of FIG. 3 or a different system. For example, a beamformer and transducer of an ultrasound system are used for act 12. A contrast agent detector of the system performs act 14. A processor performs acts 16 and 18. The ultrasound system performs act 20. Other devices or combinations of devices may be used for any of the acts.

The acts are performed in the order shown or another order. As shown, act 12 is performed for each type of contrast agent detection before then performing act 14 for each type of contrast agent detection. In another order, acts 12 and 14 are performed in series for one type of contrast agent detection, and then repeated for another type before performing act 16.

Additional, different, or fewer acts may be provided. For example, acts for configuring the ultrasound system to perform contrast agent imaging are added. As another example, the feedback from act 20 to act 12 for repetition is not provided.

In act 12, a region of the patient is scanned. The scanning is with ultrasound. A transmit beamformer generates electrical waveforms for different elements. The waveforms are relatively delayed or phased and apodized to focus an acoustic transmit beam or beams along one or more scan lines in a patient. The electrical waveforms are applied to a transducer, which converts the waveforms into acoustic energy. The acoustic energy propagates into the patient. Echoes from the acoustic energy are received by the transducer. The transducer converts the received acoustic energy into electrical receive signals at each element. A receive beamformer delays or phases and apodizes the signals to form a receive beam of samples representing the acoustic response along each of one or more scan lines per transmit beam. By repeating the transmission and responsive reception along different scan lines or groups of scan lines, a region of the patient is scanned.

For each image to be generated, a given scan line is scanned one or more times. The resulting image represents the contrast agent at a time or for a scan period. The scanning is repeated for other times or periods.

The region may include contrast agents. Contrast agents are microspheres filled with gas. Other now known or later developed contrast agents for medical ultrasound imaging may be used. The contrast agents are injected into the blood of the patient and travel within the circulatory system. Some of the contrast agents may perfuse into tissue. The scan of the region with contrast agents is to detect the contrast agents. Other scans for detecting tissue or blood may also be performed, such as using interleaving with other scanning modes.

The scan for contrast agents is specific for contrast agent detection. For example, two or more pulses or beams are used for a same scan line. As another example, the two or more pulses have different amplitudes and/or phasing. Alternatively, a single pulse or beam is used to determine contrast agent response. The pulses for a given type of contrast agent imaging are transmitted in the scan. Since two or more types of contrast agent imaging are tested, the pulses for the two or more types of contrast agent imaging are transmitted.

In one embodiment, the different types of contrast agent imaging share responses from one or more pulses. In order to reduce the amount of time to acquire the information for detecting contrast agents using different types of detection, the scanning is arranged so that all or at least some of the responses are used in all or multiple of the types of detection. A contrast pulses sequence for one type of contrast agent detection is modified to allow the creation of contrast agent images for that type and another type from the same data collection.

In one example, the pulse sequences are for imaging a cubic fundamental response of contrast agents and a second or even harmonic response. For the cubic fundamental, three or more pulses are transmitted with different phase and amplitude, such as represented by [−1 2 −1] (e.g., three pulses where the first and third pulses are 180 degrees ("−") out of phase with the second pulse and the second pulse is twice the amplitude of the other two pulses. The responses are summed on receive with equal weighting. For the second or even harmonic, two pulses are transmitted with a same amplitude but opposite phase (e.g., [1 −1]). On receive, the responses to the two pulses are summed with equal weighting. Other sequences for either type of contrast agent imaging may be used, such as equal amplitude and/or phasing on transmit but weighted and/or phased receive.

The sequences of the two types do not, by themselves, have sufficient responses to both types. The sequences are combined or modified to share information. For example, a fourth pulse is added to the cubic fundamental pulse sequence to provide for the second harmonic sequence, such as [−1 2 −1 1]. The cubic fundamental uses the responses from the first three pulses and the second harmonic uses the responses from the last two pulses. The response from the third pulse is shared by both types of contrast agent imaging.

A greater amount of overlap, reducing the number of pulses needed for two or more types of contrast agent imaging, may be provided. The cubic fundamental sequence is repeated over time. Rather than each repetition being identical (e.g., [−1 2 −1/−1 2 −1/−1 2 −1 . . . ]), the phase is changed by 180 degrees for each repetition. For example, the sequence has at least three pulses with at least two amplitudes and at least one phase difference, but each repeat is 180 degrees out of phase (i.e., opposite phase or modified triplet with inverted phase) with the previous sequence. One embodiment is provided as [+1 −2 +1/−1 +2 −1/+1 −2 −1/ . . . ]. Multi-beam receive is used so that the response from multiple scan lines is received in response to each pulse. As a result, one scan line may have responses received from different pulses. The cubic fundamental response is formed by adding the triplets at each lateral location [−1 +2 −1] for one location and [1 −2 1] for another. The second harmonic uses the same pulses and response, such as [−1 1] and [1 −1] for the two lateral locations.

Another example sequence with overlapping information uses pulses with opposite phase, but implements apodization or relative amplitude with a size or number of elements used in the transmit aperture. Instead or in addition to transmitting pulses with different amplitude due to amplification or electrical waveforms with different amplitude, the acoustic pulse amplitude is varied using the transmit aperture size. For example, a 4-pulse sequence is formed, where groups of even, e, and odd, o, elements are switched on and off to provide the amplitude modulation pattern. Rather than repeat every three pulses as inverted, the sequence is [+1 o −2 +1 e +2/+1 o −2 +1 e +2/ . . . ]. In this sequence, the cubic fundamental response is formed using the first three pulses, but then the second harmonic response is formed with the [−2 +2] firings from the sequence. Other element groupings may be used to set the amplitude of the acoustic pulses without using different amplitude of the electrical transmit waveforms.

Other sequences may be used for the cubic fundamental and/or second harmonic responses. Other or the same sequences may be used for other types of contrast agent detection.

In act 14, a detector of the ultrasound imaging system detects the contrast agents. The response from contrast agents is detected by filtering, summation, phasing, subtraction, or other process to isolate contrast information from information from tissue or blood. The isolation may be partial (e.g., less specific). The detection is from ultrasound data resulting from the scanning of act 12.

Two or more different contrast agent imaging techniques are used. Any of various parameters are different to provide different types of contrast agent detection. Contrast agent imaging parameters include: transmit sequence, detection technique, transmit modulation frequency, transmit bandwidth, transmit coding, number of transmit foci per scan line, number of transmit pulses per scan line, number of transmitted lines per image, time between transmissions, velocity scale, reverberation-suppression pulses, receive bandwidth, receive demodulation frequency, pre-detection gains, and post-detection gains. Other now known or later developed contrast agent imaging parameters may be provided, set, and altered.

The fundamental, harmonic, or fractional harmonic response of the contrast agents is detected. The received signals are filtered or combined (e.g., subtraction, addition, or weighted addition/subtraction of signals from multiple pulses) to isolate the information at the desired pass bands. The envelope or intensity of the resulting echo signals, the energy from a flow or Doppler processor or other technique is used to detect the response from the filtered and/or combined received signals.

In one type of detection, the response at a particular frequency band is detected from one pulse. Filtering is used to isolate the contrast agent response. For example, the filtering is a high pass filter removing or reducing the fundamental or transmit frequency band, leaving second, third, and/or higher harmonic bands. Filters for fractional or other harmonics specific, at least partially, to contrast agents may be used.

In another embodiment, the received signals are responsive to transmissions along the same or adjacent scan lines with different phases, such as two or more transmissions with 180-degree phase shifts. The detector combines signals representing a same or adjacent scan line by addition or subtraction. Equal or different weights may be applied to the received signals prior to combination. In other embodiments, the transmit pulses are the same, but are subtracted on receive.

In yet another embodiment, the received signals are responsive to transmissions along same or adjacent scan lines with different amplitudes. The received signals may or may not also be associated with different phases, such as 180 degrees, lesser or greater shifts, for one or more received lines. The detector combines the received signals using equal or unequal weights, such as with a finite impulse response filter.

In one embodiment, three separate waveforms are transmitted with a same phase and amplitude (e.g., [1 1 1]). Fewer or a greater number of pulses may be used for each detected datum. The detector weights the received data, such as with a [1 −2 1] filter.

In another embodiment, the received signals are responsive to two or more transmissions along same or adjacent scan lines with a same amplitude and/or phase. When contrast agents are destroyed or disrupted during two or more different transmit events, the received data have a loss-of-correlation (LOC). The second data is different than the first data. The change in response is detected.

Other loss of correlation detection sequences are possible. For example, many sequences used for traditional color flow imaging provide loss of correlation detection in addition to detection of motion (correlated or partially correlated). Sequences that detect motion with imaging modes such as color Doppler velocity (CDV) or color Doppler energy (CDE) also detect loss of correlation. Detectable energy or velocity originates from differences between two or more pulses. Other methods using two or more receive pulses after two or more pulses are transmitted can be used.

Contrast agent detection techniques may be based upon detecting an increase in signal strength or a decrease in signal strength. When contrast agents are destroyed by one pulse, a second pulse may not echo from any contrast agent. The returned signal is less for the second pulse. In one embodiment, the detector detects contrast agent from one or more received signals after pulses are transmitted for destroying the contrast agent.

In a further example of different types of contrast agent detection, power modulation, phase inversion, power pulse inversion, pulse inversion, power harmonics, sub- or ultra-harmonics, or similar transmit sequences and detection are provided.

Other types of contrast agent detection include detection of the cubic fundamental response. Each transmit sequence is defined, at least in part, by a number of pulses, a phase of pulses and an amplitude of pulses. For example, multiple transmit pulses are provided with inter-pulse amplitude and phase modulation (e.g., [0.5 −1 0.5]). Interpulse amplitude and phase modulation allows detection of nonlinear signals from contrast agents and proper receive filtering may suppress tissue signals and isolate contrast signals from tissue signals. Any nonlinear detection technique may be used, such as discussed above for the scanning for cubic fundamental response.

Any two or more types of contrast agent detection are performed. The differences are in the scanning, the combination, and/or other parameter. In one example, the cubic fundamental and plus inversion (i.e., second or even harmonic) detections are performed. By performing the different types of detection, the sensitivity and/or specificity resulting from the detections may be different In another approach, the different types of contrast agent detection use the same pulse sequence. Different receive baseband filtering with different center frequency, different bandwidth, or both are used to distinguish the different responses, providing the different techniques. Adaptive backend processing (e.g., receive baseband filtering parameters—center frequency, filter bandwidth, or others) generates the two images from the same datasets. For example, a three pulse cubic fundamental transmit pulse sequence (i.e. [1 −2 1]) and receive weighting of [1 1 1] are used. The different types of detection are provided by altering the center frequency and baseband filter bandwidth to produce both the non-linear (cubic) fundamental response and the second harmonic response from the received sequence or combined signals.

The detection provides data representing contrast agents. Since two or more types of detection are performed for the same locations and/or region of the patient, two or more data sets representing contrast agent response at a given time or period are provided. The different types of contrast agent detection result in different response information from any contrast agents in the scan region.

In act 16, the detected responses of the contrast agents are compared. A processor compares the responses from the two or more different contrast agent imaging techniques.

Any measure may be used for comparison. For example, the comparison is of the contrast agent sensitivity. The technique resulting in a greater contrast agent return or detection is identified. The sensitivity may be measured as the signal-to-noise ratio of the data. In another embodiment, the sensitivity is measured by thresholding. Signals below a threshold level are zeroed or assumed not to be from contrast agents. The remaining signals are summed, averaged, or otherwise combined as a measure of sensitivity. In yet other embodiments, other measures, such as a maximum signal, number of locations with response, or combinations of measures, may be used.

The comparison is between the measures. The contrast agent technique with the greatest or larger sensitivity or other characteristic is determined. A minimum or other comparison criterion or criteria may be used. The comparison provides a priority or ranking of one technique relative to other techniques for a given time and patient.

In act 18, a relative contribution of the different contrast agent imaging techniques is selected. A processor selects the relative contribution based on the comparison of act 16. The selection is of the technique to use for contrast agent imaging in act 20. The relative contribution of each of the multiple techniques to the contrast agent imaging is selected.

In one embodiment, the selection is of just a single contrast agent imaging technique. Where the responses from two or more techniques are compared, only one technique is selected. The other technique or techniques are not used. For a relative contribution, one technique provides all of the contribution and another technique provides none of the contribution.

In another embodiment, the relative contribution is not binary or not of only one technique. More than one technique is selected. All of the techniques or just a sub-set of the techniques are selected. For the selected techniques, the relative contribution is more than none and less than all. The relative contribution is a ratio of the different contrast agent imaging techniques less than 1.0 and more than 0.0. Any linear or non-linear weighting may be applied to establish the ratio. For example, the weight applied to each technique for setting relative contribution is based on the difference in sensitivity or priority from the comparison. Other mapping of the comparison results to relative weights may be used.

In act 20, contrast agent imaging is performed using the selected contrast agent imaging technique or techniques. The ultrasound imaging system generates one or more contrast agent images. The image is output to a display and/or memory.

The generated image uses the data from the scan of act 12. The already acquired data is used to generate a one, two, or three-dimensional image. Alternatively or additionally, subsequent scanning, detection, and imaging are performed using the selected technique or techniques.

The contrast agent imaging is performed based on the selected relative contribution. Where only one technique is selected, the contrast agent imaging is performed using the technique. For example, a cubic fundamental technique is selected. The image is of the cubic fundamental response. Subsequent imaging may be of the cubic fundamental response as well. Other techniques are not used to generate one or more images.

Where the relative contribution includes contribution from two or more techniques, one or more images include information from the multiple techniques. The responses from the different techniques are combined in imaging. Any combination may be used. For example, the data for one technique is mapped to a color scale, and the data from another technique is mapped to a different color scale or gray scale. The data from the technique with the greater relative contribution uses a color or other mapping indicative of the greater contribution, such as a brighter or more distinctive coloring. As another example, the data from the different techniques is combined by weighted averaging. The weights used are the relative contribution or are determined from the relative contribution. For each location, a weighted average from the responses for the different techniques is performed. The resulting value or intensity is used for the image, such as to modulate the gray scale intensity or color.

The combination is a function of the relative contribution. The weights, mapping, or other imaging characteristic is determined from the relative contribution. For example, the data from the technique with the greater contribution is weighted more.

Any number of images is generated based on the relative contribution and corresponding selected techniques. In one embodiment, the comparison and selection are performed once in an examination. The subsequent imaging uses the selected technique or techniques and relative contribution for the remainder of the examination or at least until the user triggers repetition. The subsequent imaging includes scanning just for the selected technique or techniques without pulses needed for non-selected techniques.

In another embodiment, the contrast agent imaging is performed using only the already acquired data and the process is repeated to acquire the next image. By repetition of acts 12-20, the selected technique or techniques and corresponding image is updated to account for any change in conditions, such as contrast agent concentration.

Any number of images may be generated before the repetition of acts 12-18. More than only one and less the all the rest are generated. For example, the contrast agent imaging and corresponding scanning and detection for the selected technique or techniques are performed repetitively to generate one or more images. The acts for selecting the technique or techniques (e.g., acts 12-18) are repeated periodically, such as every two seconds, five seconds, twenty seconds, or other period.

Alternatively, the ongoing images are used to trigger repetition, such as triggering when an average contrast agent signal deviates by a percentage or amount from an initial average. Other triggers may be used.

Whether using a timer or adapting to contrast agent information, the repetition to select is constant or is sparse relative to the repetition of scanning and imaging for the selected contrast agent technique or techniques. Where the repetition is sparse, the selected contrast agent technique or techniques are used to scan and generate contrast agent images until the next repetition. The special sequence of acts 12-18 may take longer to collect and process since the scanning and detection may be performed for a greater number of techniques and/or involves the comparison not normally performed during contrast agent imaging. The repetition of acts 12-18 is used infrequently for only measuring contrast agent image sensitivity. Once the selection is made again in act 18, the contrast agent imaging of act 20 uses just the transmit sequence needed for the selected technique or techniques (e.g., either a 3-pulse or 2-pulse for cubic fundamental or second harmonic, respectively, is used the rest of the time). In this fashion, the frame rates may be greater than with repetition that is more frequent.

The repetition occurs one or more times during an imaging session of the patient. For a contrast agent-based examination of a patient, a transducer is selected, the ultrasound system configured, contrast agent injected, and patient acoustically scanned for the contrast agents. The imaging session may last until the contrast agent is no longer detected. The ultrasound scanning ceases due to the sonographer stopping the ultrasound system. The examination may be repeated with injection of additional contrast agent. At some point, the appointment for the patient for the particular imaging session ends, such as after thirty minutes to an hour. The imaging session is for a particular patient's appointment and/or start to finish imaging of a patient over a continuous period. During this imaging session and after start of the scanning, the method of FIG. 1 is performed and then repeated at least once.

Figure 2:
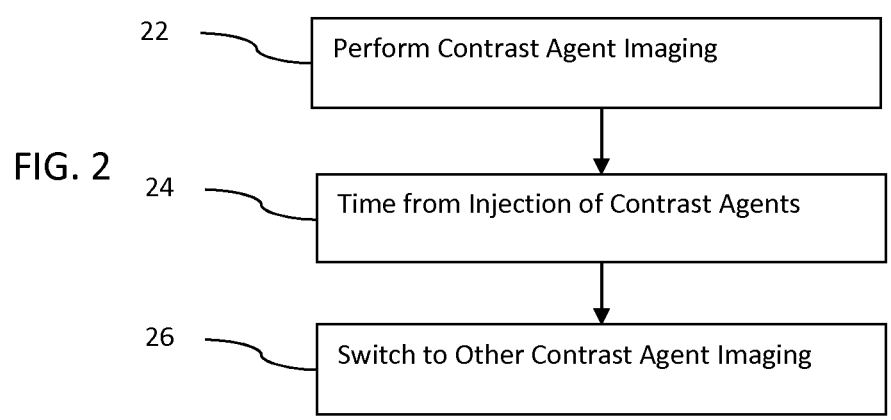
FIG. 2 is a flow chart diagram of another method for medical ultrasound imaging of contrast agents.

FIG. 2 shows a flow chart for an alternative method for medical ultrasound imaging of contrast agents. Rather than adapting to the sensitivity as measured during the imaging session, the sensitivity may be assumed. Using the known or likely sensitivity of two or more techniques and the known or likely progression of contrast agents in a patient, the technique is switched based on timing.

Additional, different, or fewer acts may be provided. For example, the timing-based switch of FIG. 2 may be used with acts of the sensitivity measure-based switch of FIG. 1. Timing is used to make one switch, but measures from scanning are used to make another switch during the imaging session. In another example, acts for injecting contrast agent, configuring the ultrasound system, and/or positioning the transducer are performed. The acts are performed in the order shown or a different order.

In act 22, an ultrasound system performs one type of contrast agent imaging. At some point in the imaging session, such as starting just prior to and/or during inflow of contrast agent into a scanned region, the patient is scanned and images generated using a technique for contrast agent imaging.

Any technique or a combination of techniques may be used. For example, the scanning, detecting, and imaging use the cubic fundamental response of the contrast agents. In one embodiment, only the cubic fundamental response is used. The scanning uses transmission of pulses with different amplitudes and phases. On receive, the combination of responses to the pulses isolates or enhances information at the cubic fundamental relative to other frequencies. The cubic fundamental response is detected and used to generate a grayscale or color image.

In another embodiment, the contrast agent imaging is performed for two or more contrast agent imaging techniques. The data from detecting using the different types of contrast agent imaging are blended. The relative contribution for the combination is pre-determined, such as weighting the cubic fundamental data more greatly than weighting second or even harmonic data. The weighted data is then summed in a weighted average. The weighted averaging is performed for each location of various contrast agent locations in the scan region. Other blending or combination may be used, such as combining using different color schemes in imaging.

In act 24, the imaging session is timed. A timer determines an amount of time from initiation of the timer. A difference between two times may alternatively be used.

The timing is relative to an injection of the contrast agent into the patient. The timer starts upon injection. The user may trigger the timer before, as, or after the contrast agent injection begins. Alternatively, the injection pump communicates with the ultrasound system, which starts the timer in response to an injection signal from the pump.

In other alternative embodiments for timing relative to the injection, the timer is started when contrast agents reach the scan region. The user manually activates the timer upon seeing the contrast agents using the contrast agent imaging of act 22. Instead of manual activation, automatic activation is provided where the ultrasound system measures the contrast agent response (e.g., sum or average of contrast agent signals) to be above a threshold level. Once sufficient contrast agent is detected, the ultrasound system starts the timer. In yet other embodiments, a change in contrast agent level is used, such as triggering the timer once the contrast agent level from the injection begins to decrease from a peak (e.g., wash out begins).

The timer controls switching the contrast agent imaging. When the time expires by reaching a count or by reaching an amount of time since initiation, the switch is activated. Any period may be timed. The timing is based on the expected transition in sensitivity of the different contrast agent imaging techniques. For example, the sensitivity of the cubic fundamental begins to decrease upon the start of wash out or upon the amount or concentration of contrast agent going below a given level. The second harmonic sensitivity is better than the cubic fundamental at a certain point. Rather than measuring the sensitivity, the time from the initiation of the timer to a prediction of the switchover in relative sensitivity is estimated. The timer indicates the estimated time.

Any amount of time is estimated. In one embodiment, the time is at a point after a halfway time of contrast agent presence. The halfway time may be estimated based on the type of contrast agent, the patient, the region of the patient being examined, and/or other information. Rather than the halfway time, the time of peak concentration, a last third, a time of wash-out beginning, or other time may be estimated.

The phase of the contrast agent imaging is timed and used to switch between types of contrast agent imaging. For example, in an early phase, only the cubic fundamental image or an image blended from two or more techniques with the cubic fundamental or other type more heavily weighted is shown. In a late phase of the contrast agent progression, the second harmonic image or a blended image with the second harmonic more heavily weighted is shown.

In act 26, the ultrasound system switches to a different type of contrast agent imaging. In response to the timer reaching the desired time or period, the ultrasound system automatically changes the type of contrast agent imaging being performed. The switch occurs during the imaging session, such as at the estimated time of decrease or poor sensitivity using the initial type of contrast agent imaging.

A different type of contrast agent imaging is used upon the switch. For example, the ultrasound system switches to scanning, detection, and imaging using the second or even harmonics. The type of contrast agent imaging used after the switch is just the second or even harmonic approach. Alternatively, the same techniques are used, but the relative contribution switches. For example, the data of the second harmonic technique transitions from being weighted less than the data of the cubic fundamental to being weighted more. In other alternatives, the combination of techniques switches, such as replacing, adding, or removing one or more techniques.

FIG. 3 shows a system 50 for ultrasound imaging of contrast agents. The system implements the method of FIG. 1, FIG. 2, or both. Alternatively, other methods for switching between types of contrast agent imaging based on measured or predicted sensitivity during an imaging session are implemented by the system 50.

The system 50 includes a transducer 54, a transmit beamformer 52 with a transmit amplifier 53, a receive beamformer 56, a detector 58, a memory 64, a processor 62 and a display 60. Additional, different or fewer components may be provided, such including multiple detectors associated with contrast agent, B-mode, and flow or Doppler imaging. As another example, a scan converter is provided to format the acquired polar coordinate data into data in a Cartesian coordinate format for the display 60. The system 50 is a medical diagnostic ultrasound system from any of various manufacturers.

The transducer 54 is a single element or multiple elements of piezoelectric material. In alternative embodiments, the transducer 54 has capacitive membrane structures. For multiple elements, the transducer 54 is a linear, curved linear or multidimensional array. Other transducers for converting between electrical and acoustic energy can be used. The transducer 54 outputs acoustic waveforms at powers set by the transmit amplifier 53. The acoustic waves are transmitted along one or more scan lines in response to settings of the transmit beamformer 52. The transmitted waves have amplitudes, phases, center frequencies, bandwidth, coding and foci also set by the transmit beamformer 52. The number of times the acoustic waveforms are transmitted along a given scan line and pulse repetition interval is also set by the transmit beamformer 52.

The transmit beamformer 52 includes one or more waveform generators, sample memories, oscillators, delays, phase rotators, filters, transmit amplifiers 53, digital-to-analog converters, other digital components, analog components and any other now known or later developed transmit beamformer components. The transmit beamformer 52 is configured into one or more channels for generating one or more electrical waveforms with relative delays and apodization for scanning a region of a patient. The waveforms of each channel have an amplitude, relative phase as compared to other waveforms of other channels or of the same channel at a different time, center frequencies, bandwidth (e.g., number of cycles and type of waveform) and coding (e.g. chirp or no chirp for frequency coding). The relative delays and apodization of the waveforms across the various channels provides for one or more foci along a given scan line or across multiple scan lines for a given transmit event or for sequential transmit events. The waveforms are generated for transmissions along one or more scan lines in response to settings of the transmit beamformer 52. The number of times the acoustic waveforms are transmitted along a given scan line and pulse repetition interval is also set by the transmit beamformer 52.

The transmit amplifier 53 connects with the transducer 54 and is a variable amplifier, digital-to-analog converter or other analog or digital device for changing or increasing a power, peak voltage or other power characteristic of a transmit waveform. In alternative embodiments, the transmit amplifier 53 comprises a voltage divider or other device for reducing the power associated with the transmit waveform. A separate transmit amplifier 53 is provided for each transmit beamformer channel or transducer element, but one transmit amplifier 53 may be used for a plurality of channels or elements. In one embodiment, the transmit amplifier 53 applies apodization for transmitting along a beam and is included as part of a transmit beamformer 52.

Using the transmit amplifiers 53 and the transducer 54, the transmit beamformer 52 generates a sequence of pulses or transmit beams for contrast agent scanning. The sequence of pulses along a given scan line or adjacent scan lines has a same or different amplitude and/or relative phasing. For example, the amplitude varies using the amplifiers 53 and/or aperture selection (e.g., even or odd channels). The phase varies using different relative delays or phasing in generating the sinusoidal or cyclical waveforms. One transmission may start with the waveforms going from a zero value upwards and a subsequent transmission may start with the waveforms going from the zero value downwards. In alternative embodiments, a single pulse is transmitted along a given scan line at a desired amplitude for contrast agent imaging.

The transmit waveforms output from the transmit amplifier 53 are converted to acoustic energy by the transducer 54. Echo signals responsive to the acoustic energy and any contrast agents are received by the transducer 54. The transducer 54 converts the echo signals into electrical signals or data. Data includes one or more digital samples or analog information. The echo signals are provided to the receive beamformer 56.

The receive beamformer 56 includes amplifiers, channel filters, phase rotators, multipliers, analog-to-digital converters, summers, post-sum filters, memories, buffers, demodulator, digital components, analog components and any other now known or later developed receive beamformer components. The receive beamformer 56 is configured into one or more receive channels connected with one or more transducer elements. The receive channels apply relative delays, apodization and weighting as a function of channel for focusing along the scan lines. The receive channel data is summed together to form beamformed data. Using filters in the channel or after the summer, the bandwidth of the data is adjusted. The demodulator demodulates to one or more receive frequencies, such as fundamental, fractional harmonics (e.g., 1.5 harmonic), second harmonic, or other harmonics of the fundamental transmitted frequency. The receive pre-detection gain, such as the dynamic range, noise floor and other gain adjustments are also implemented by the receive beamformer 56. The receive beamformer 56 outputs samples or data responsive to the pulses of the transmit sequence. The samples are output for one or more depths along each of one or more laterally and/or elevation-spaced scan lines.

The receive beamformer 56 and/or the contrast agent detector 58 may include one or more buffers, phase rotators, multipliers and/or summers. A finite impulse response filter or processor may be used. The buffers store samples for a given location responsive to different pulses. The samples are phase rotated, weighted, and/or summed for each location. The combination of samples responsive to the different pulses allows for multiple pulse-based techniques for contrast agent detection, such as providing for summing samples from two or more pulses to isolate information at a desired frequency band.

The detector 58 is a loss of correlation detector, B-mode detector, Doppler detector, flow detector, or other contrast agent detector. Any of the contrast agent detection techniques described above may be used. In one embodiment, the detector 58 is used for imaging contrast agents as well as B-mode and F-mode detection. Alternatively, the detector 58 is used for contrast agent detection separate from other detectors for other types of imaging. The detector 58 detects signals responsive to contrast agents, such as fundamental or harmonic signals, contrast agent destruction, loss of correlation due to flow or destruction, or other now known or later developed contrast agent detection technique.

In one embodiment, the detector 58 detects responses from the samples using different processes. The processes for different techniques are performed in sequence or in parallel. The contrast agent response is detected using different types of detection. The responses from the different types of detection may use separate, the same, or overlapping samples. For example, each of the processes uses at least one of the same samples for a given location.

In an example, the detector 58 detects using a cubic fundamental process and detects using a second harmonic process (e.g., only second harmonic, second and greater harmonics, or even harmonics). The detection occurs for both processes to measure sensitivity. Alternatively or at other times, the detection for one process is performed for a period and the detection for the other process is performed for a different period. During contrast agent imaging at a given time, only one process or combinations of processes for contrast agent detection are implemented by the detector 58. A different process, different combination of processes, or different weighting of the contribution of processes is implemented by the detector 58 during contrast agent imaging at another time.

The processor 62 is an application specific integrated circuit, a general processor, a digital signal processor, a control processor, a field programmable gate array, a digital circuit, an analog circuit, combinations thereof, or another device operable to vary the processes used for contrast agent imaging based on time and/or detected sensitivity. The processor 62 is part of the ultrasound system 50, but may be a separate computer or server in other embodiments.

The processor 62 is configured by hardware, software, and/or firmware to cause the ultrasound system 50 to implement different types of contrast agent imaging at different times. The processor 62 performs some acts, such as comparing, selecting, and/or timing. The processor 62 may cause other components of the ultrasound scanner to perform other acts, such as causing the beamformers 52, 56 and detector 58 to implement one or more processes for contrast agent detection.

The processor 62 is configured to cause scanning to acquire contrast agent data for different processes, measure sensitivity or other characteristic, compare the responses, and select one or more processes to use for imaging. Alternatively or additionally, the processor is configured to time relative to injection of contrast agent and switch the process for contrast agent imaging based on the timing.

In one embodiment, the processor 62 is configured to generate contrast agent images where a ratio of the responses from the samples of the different processes in the contrast agent images varies. The ratio may be binary, such as using one process at one time and a different process at another time. The ratio may result in blending or other combination of data for imaging from more than one of the processes at a time.

The processor 62 is configured vary the ratio as a function of relative sensitivity to the contrast agents of the responses of the different processes. The measures or calculated sensitivity determined by the processor 62 is used. Alternatively, other measures of relative contrast agent response than sensitivity are used. In yet other embodiments, the processor 62 varies the ratio based on a timer using an assumed or estimated relative sensitivity.

The memory 64 is a cache, buffer, RAM, or other memory accessed by the processor 62 and/or other components of the system 50. The memory 64 stores measures of sensitivity, timing information, selections, or other information. Pulse sequence, detection, or other control information for performing different processes for contrast agent imaging using different techniques are stored for use by the system 50 to perform contrast agent imaging.

Alternatively or additionally, the memory 64 is a computer readable storage medium having stored therein data representing instructions executable by the programmed processor for contrast agent imaging in medical diagnostic ultrasound. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 60 is a monitor, LCD, LED, plasma, projector, printer, or other now known or later developed display device. The processor 62 and/or the contrast agent detector 58 generate display signals for the display 60. The display 60 is configured to display an image representing the contrast agent response in the scanned region of the patient. The image is generated from data of one or more contrast agent imaging techniques. A sequence of images representing the patient over time is displayed. The images of the sequence are responsive to different relative contributions of two or more different processes for contrast agent imaging. By altering one or more contrast agent imaging parameters, different contrast agent response is detected. The resulting images have different sensitivity and/or specificity at different times due to variation in the process of contrast agent imaging.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for medical ultrasound imaging of contrast agents, the method comprising:
   scanning, by a beamformer and transducer, a region of a patient having contrast agents;
   detecting, by a detector, the contrast agents with at least two different contrast agent imaging techniques from ultrasound data resulting from the scanning;
   comparing, by a processor, responses of the contrast agents detected between the at least two different contrast agent imaging techniques;
   selecting, by the processor, a contribution of the at least two different contrast agent imaging techniques, the selecting being based on the comparing; and performing contrast agent imaging of the patient using at least one of the contrast agent imaging techniques, the performing being based on the selected contribution,
wherein comparing responses comprises comparing contrast sensitivity,
wherein selecting comprises selecting the contribution as a ratio of the at least two different contrast agent imaging techniques less than 1.0 and more than 0.0, and wherein performing comprises generating a contrast agent image as a combination of information from each of the at least two different contrast agent imaging techniques with the combination being a function of the contribution.

2. The method of claim 1 wherein scanning comprises scanning with a repeating sequence of pulses where response from at least one pulse is used for detecting the contrast agents for each of the at least two different techniques.

3. The method of claim 2 wherein the sequence of pulses comprises three pulses with at least two amplitudes and phase differences and a repeat of the three pulses with opposite phase.

4. The method of claim 2 wherein the sequence of pulses comprises pulses with opposite phase using a full aperture separated by pulses having a same phase using less than the full aperture.

5. The method of claim 1 wherein detecting comprises detecting a cubic fundamental response of the contrast agents and detecting a second harmonic response of the contrast agents as the at least two different techniques.

6. The method of claim 1 wherein detecting comprises receive baseband filtering with different center frequency, different bandwidth, or both as the at least two different techniques.

7. The method of claim 1 wherein scanning, detecting, comparing, selecting, and performing are repeated during an imaging session for the patient, where the contribution varies during the imaging session due to the repetition and change in responses of the contrast agent.

8. The method of claim 7 wherein the repetition of the selecting is sparse relative to the repetition of the scanning, detecting, and performing.

9. The method of claim 1 wherein selecting comprises selecting the contribution as just one of the at least two different contrast agent imaging techniques, and wherein performing comprises performing the contrast agent imaging using just the one contrast agent imaging technique.

10. The method of claim 1 wherein performing the contrast agent imaging comprises generating an image of the contrast agent on a display.

* * * * *